US005480410A

United States Patent [19]
Cuschieri et al.

[11] Patent Number: 5,480,410
[45] Date of Patent: Jan. 2, 1996

[54] EXTRACORPOREAL PNEUMOPERITONEUM ACCESS BUBBLE

[75] Inventors: Alfred Cuschieri, Fife, Scotland; Malcom D. Heaven, Hopewell, N.J.

[73] Assignee: Advanced Surgical, Inc., Princeton, N.J.

[21] Appl. No.: 209,278

[22] Filed: Mar. 14, 1994

[51] Int. Cl.$^6$ .................................................. A61B 17/04
[52] U.S. Cl. .......................... 606/213; 606/201; 606/215
[58] Field of Search ..................................... 606/213, 215, 606/93–96, 201–203; 604/167, 174, 178, 256, 237; 128/DIG. 26; 248/56; 272/34, 34.3

[56] References Cited

U.S. PATENT DOCUMENTS

| | | |
|---|---|---|
| 3,480,017 | 11/1969 | Shute ........................................ 606/191 |
| 4,092,010 | 5/1978 | Carlson, Jr. . |
| 4,241,735 | 12/1980 | Chernov ................................ 606/191 X |
| 5,108,420 | 4/1992 | Marks ....................................... 606/213 |
| 5,137,520 | 8/1992 | Maxson et al. . |
| 5,167,637 | 12/1992 | Okada et al. ............................ 604/167 |
| 5,176,648 | 1/1993 | Holmes et al. . |
| 5,192,301 | 3/1993 | Kamiya et al. ......................... 606/213 |
| 5,211,370 | 5/1993 | Powers . |
| 5,215,531 | 6/1993 | Maxson et al. . |
| 5,366,478 | 11/1994 | Brinkerhoff et al. .................. 606/213 |

Primary Examiner—Stephen C. Pellegrino
Assistant Examiner—Michael Peffley
Attorney, Agent, or Firm—Burns, Doane, Swecker & Mathis

[57] ABSTRACT

A medical device for forming an external extension of the pneumoperitoneum, thus allowing the surgeon more flexibility in a surgical procedure. The device includes an enclosure and an elastically deformable flange or ring at an open end of the enclosure. The flange/ring is deformed and inserted into a trocar puncture site, upon which it deploys against the inner surface of the abdominal wall. By maintaining a gentle lifting force on the external portion of the device (this being essentially a balloon shape) the neck of the device forms a seal between the opening in the abdominal wall and the 'balloon', allowing the insufflation gas to inflate the external 'balloon' or 'bubble' portion of the device. Once inflated, the internal pressure maintains the device in a stable shape. The device includes one or more valved openings which allow access to the interior of the balloon, and hence the abdominal cavity. These openings may be small, allowing access of laparoscopic instruments through the valve, or somewhat larger, allowing the access of a hand or hands. The valve design minimizes loss of pneumoperitoneum.

24 Claims, 3 Drawing Sheets

EXTRACORPOREAL PNEUMOPERITONEUM ACCESS BUBBLE

FIELD OF THE INVENTION

The present invention relates to improvements in laparoscopic procedures enabled by the use of a device which effectively extends the pneumoperitoneum extracorporeally. The device allows the use of a broader range of instruments, including conventional surgical instruments, and even the direct interaction of the surgeons hands without loss of insufflating gas.

BACKGROUND OF THE INVENTION

Laparoscopic surgery (laparoscopy) is becoming a preferred method for performing various types of surgical operations. However, unlike other types of surgical procedure, s, laparoscopic surgery does not require large incisions to expose the internal organs. Instead, an insufflation needle, typically a Veress needle, is inserted into the abdominal cavity, and an insufflation gas such as $CO_2$ used to inflate the cavity. Once safely inflated a trocar is inserted through the original puncture site. On removal of the trocar knife a laparascope may be inserted through the cannula left insitu, allowing visualization of the interior of the abdomen and safe insertion under direct visualization of further trocars/cannulas as needed. Access for surgical instruments is now available through these extra cannulas. In order to prevent escape of pressurized gas from the body cavity, instrument supporting devices have been proposed in U.S. Pat. Nos. 5,137,520; 5,176,648; 5,211,370 and 5,215,531.

Several problems are associated with the sheath, cannula or other similar devices. Such problems include limited access to the organ or organs being worked on, limits on the number of instruments and variety of instruments which can be used during a given procedure, lack of access of the surgeon's hand or hands to the body cavity, limited visibility, lack of protection of the incisions from diseased tissues, organs or cells during removal of the diseased tissues, organs or cells. Accordingly, there is a need in the art for solutions to the above problems.

SUMMARY OF THE INVENTION

The invention provides a medical device forming an extracorporeal pneumoperitoneum access bubble useful in laparoscopic surgical operations. The device includes an enclosure and deploying means at an open end thereof. The deploying means is deformable to a configuration which permits the open end of the enclosure to pass through a trocar puncture site in an abdominal wall. The deploying means also expands the open end of the enclosure beneath an inner surface of the abdominal wall. The enclosure also includes at least one access opening therein for accessing an interior of the enclosure and performing surgical operations beneath the abdominal wall or within the interior of the enclosure.

According to various features of the invention, the enclosure can be bulbous in shape and the deploying means can comprise an elastically deformable flange. Alternatively, the deploying means can comprise an elastically deformable ring surrounding the open end of the enclosure. In the case of a ring, the deploying means can comprise a coil spring. The ring can be of a springy material such as an engineering polymer, stainless steel, nickel titanium superelastic alloy, elastomer or other elastic material. In the case where the deploying means comprises a flange which is integral with the enclosure, the enclosure and/or the flange can be of a polyolefin, polyethylene terephthalate, polybutylene terephthalate, polyvinyl chloride, ionomer, polyurethane, nylon, polycarbonate, acrylic, ethylene vinyl acetate copolymer, polyvinylidene fluoride or blends thereof.

The access opening can comprise an iris valve of the fixed or adjustable type. In the case of the adjustable iris valve, the valve can include a rotatable ring which adjusts an opening through the valve. Other valve configurations known to those skilled in the art may also be used. According to a preferred embodiment of the invention, a plurality of valves are provided in the enclosure whereby a variety of tools or instruments can simultaneously be manipulated by the surgeon within a single trocar puncture site.

The enclosure can include a handle at an upper end thereof whereby the deploying means can be pulled into sealing engagement with an inner surface of the abdominal cavity. To allow viewing of the surgical operation, the enclosure can be partly or entirely of a transparent material. A constriction can be provided between the enclosure and the deploying means and the enclosure can either be gas-tight and expandable from a first configuration to a second configuration by supplying pressurized gas to the interior of the enclosure or the enclosure can be rigid and self- supporting. The constriction can be elastically deformable whereby the trocar puncture site can be stretched to a larger size by expansion of the constriction. For instance, the enclosure can be spherical in shape at the open end thereof adjacent the constriction and the constriction can form a narrow passage through which surgical instruments can be inserted into a patient's abdominal cavity.

DETAILED DESCRIPTION OF THE PREFERRED EMBODIMENTS

The medical device according to the present invention provides an extension of the pneumoperitoneum during laparoscopic procedures which allows improved access to the organ or organs being worked upon. The device also allows the simultaneous, multiple entry and withdrawal of a wide range of surgical instruments through a single incision in the abdominal wall, and may hence reduce the overall number of puncture sites needed for the procedure. The device can include means for allowing access of the surgeon's hand or hands to the pneumoperitoneum and the device can be of a transparent material which allows clear observation during the surgical procedure. The device aids in reducing the possible spread of disease, for example cancer cells, by preventing contact with the exposed tissue layers at the puncture site, thus allowing safe tissue specimen removal. Moreover, the device atraumatically expands the diameter of the puncture site by gently opening and taking advantage of the elasticity of the tissue. In addition, the device can be manufactured cheaply, with a view to being disposable.

The present invention will allow surgeons to bring the benefits of laparoscopic assisted bowel surgery to their patient by making the procedure easier and more cost efficient. The benefits include (1) a smaller incision, which contributes to significant benefits to the patient, such as less pain, shorter hospital stay, etc., (2) less morbidity by protecting the wound edges from contamination, (3) better resection and anastomosis by allowing the use of standard instruments, and palpation, and (4) an easier learning curve and more cost effectiveness, resulting from the ability to use standard instruments and the surgeon's hand.

The present invention provides a medical device which includes an enclosure and deploying means which can be inserted into a trocar puncture site. The deploying means then expands beneath the inner surface of the abdominal wall. By applying a gentle lifting force on the enclosure, the deploying means forms a seal with the abdominal wall allowing insufflation gas in the abdominal cavity to inflate the enclosure into a "balloon" shape. Once inflated, the internal gas pressure in the abdominal cavity maintains the device in a stable shape. The device includes one or more access openings which allow access to the interior of the enclosure, and hence the abdominal cavity. These openings may be small and incorporated in valve mechanisms, allowing access of laparoscopic instruments through such valves. However, in addition to or in lieu of the smaller openings, one or more somewhat larger openings can be provided in the enclosure, allowing access of a hand or hands of a surgeon. Preferably, the valve design is such that loss of pneumoperitoneum is minimized.

Figure 1:
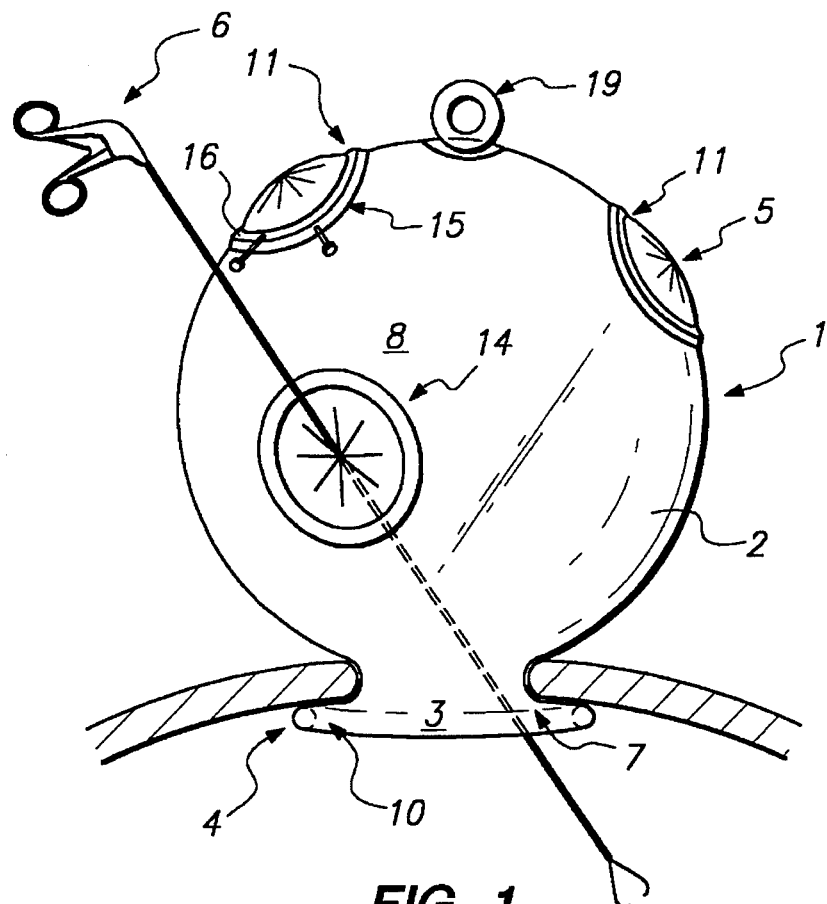
FIG. 1 shows a medical device in accordance with the invention.

FIG. 1 shows the overall construction of a device according to a preferred embodiment of the invention. The device includes a transparent enclosure 2 which forms a pneumoperitoneum extension having an open end 3 and an integral deploying means 4 at the open end 3. At least one access opening 5 is provided in the enclosure 2 for sealingly receiving a tool 6.

The enclosure 2 can be of one piece construction or sections made from different materials. For example, the enclosure 2 may consist of very thin, transparent polyolefin material, which may incorporate a slightly thicker neck section 7 to aid positioning of the device 1 in the trocar puncture site. The enclosure 2 may have a spherical shape resembling a globe or any other shape defining an empty space in the interior of the enclosure 2.

In one embodiment of the present invention, the deploying means 4 is integral with the enclosure 2 and comprises a flat annular flange 9 of springy material which aids in deploying and sealing of the device 1 on the inside of the abdominal wall. The enclosure 2 and deploying means 4 may be integrally molded from the same material, or a separate flexible flange may be incorporated into an open end of the enclosure via welding, bonding, or by any other suitable method known to those skilled in the art. For instance, the enclosure and/or deploying means may be formed via blow-molding, radio frequency welding, dipping, casting, bonding, or any other suitable method known to those skilled in the art.

Suitable materials for the enclosure and flange include, but are not limited to, polyolefins, terephthalate, polybutylene terephthalate, polyvinyl chloride, ionomers, polyurethanes, nylons, polycarbonate, acrylics, ethylene vinyl acetate copolymers, polyvinylidene fluoride, and blends and copolymers thereof.

The deploying means 4 may also comprise a separate component such as a ring 10 made from a springy material such as an engineering polymer, stainless steel, a NiTi superelastic alloy, or any other suitably springy material. For instance, the ring 10 can comprise a coil spring shaped into a ring.

Figure 2A:
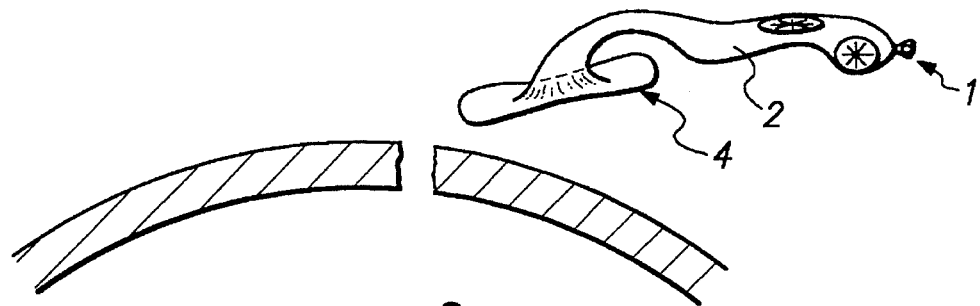
FIGS. 2a–d show ;how the medical device of FIG. 1 can be deployed in an abdominal wall of a patient.
Figure 2B:
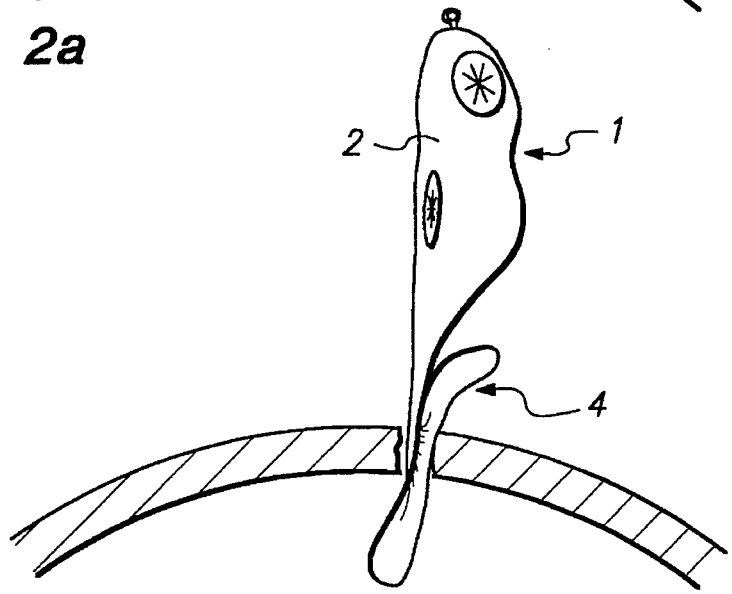
Figure 2C:
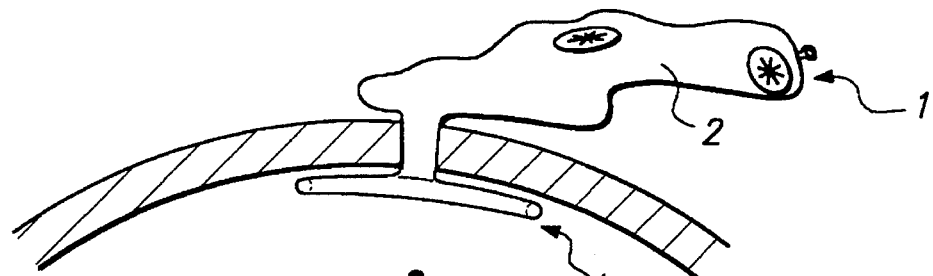
Figure 2D:
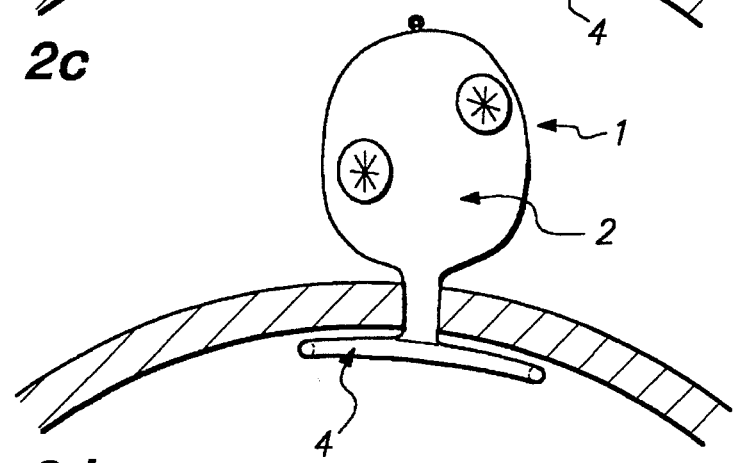

The deploying means preferably returns to its original shape after being elastically deformed by an external force. For instance, one embodiment of the present invention makes use of the elastic flange 9 or ring 10 that can be deformed (FIGS. 2a–b) by squeezing the flange/ring to ease insertion of the flange/ring into the incision. Upon insertion and release, the flange/ring will return to its original shape, as depicted in FIGS. 2c–d.

Figure 3A:
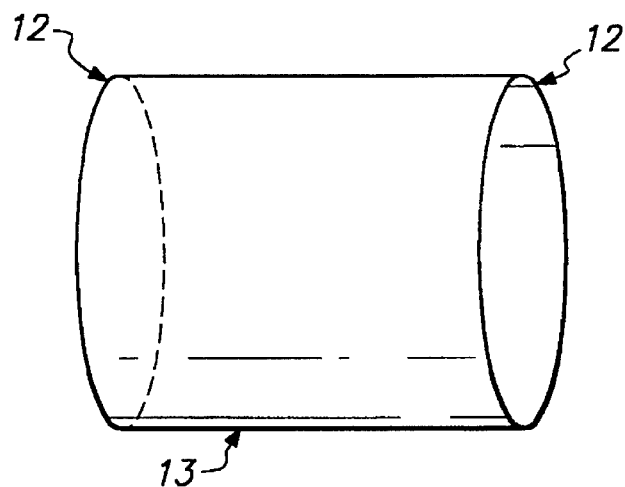
FIGS. 3a–d show details of a fixed-type iris valve which can be incorporated in the medical device according to the invention.
Figure 3C:
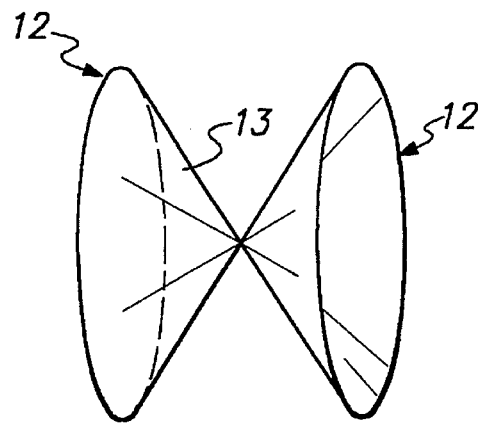
Figure 3B:
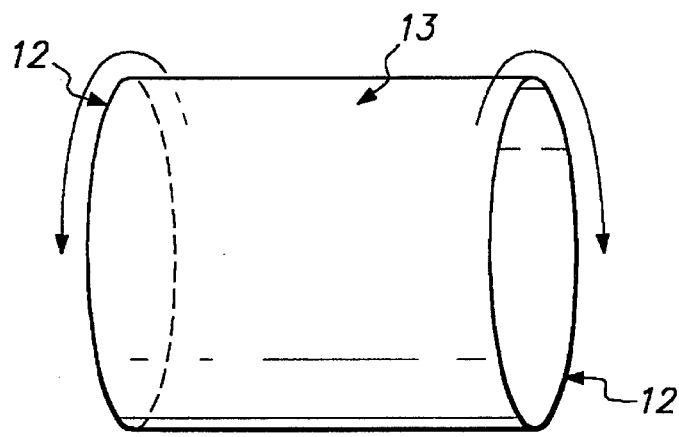
Figure 3D:
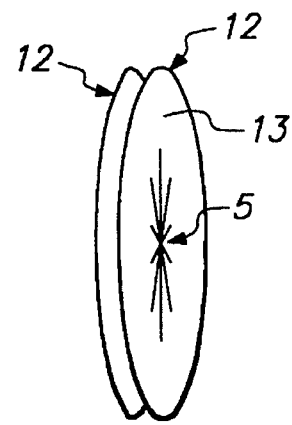

In a preferred embodiment, the access opening comprises one or more iris valves 11 constructed from a pair of rings 12 fixed or rotatable with respect to each other and connected to opposite ends of a tube 13 of an elastic material. As shown in FIGS. 3 a–d, the tube 13 can be supported at each end thereof by rings 12 and by twisting the rings 12 in opposite directions (FIG. 3b), an iris valve is formed (FIGS. 3c–d). Suitable tube materials include, for example, natural rubber, latex or polyurethane elastomers.

Figure 5:
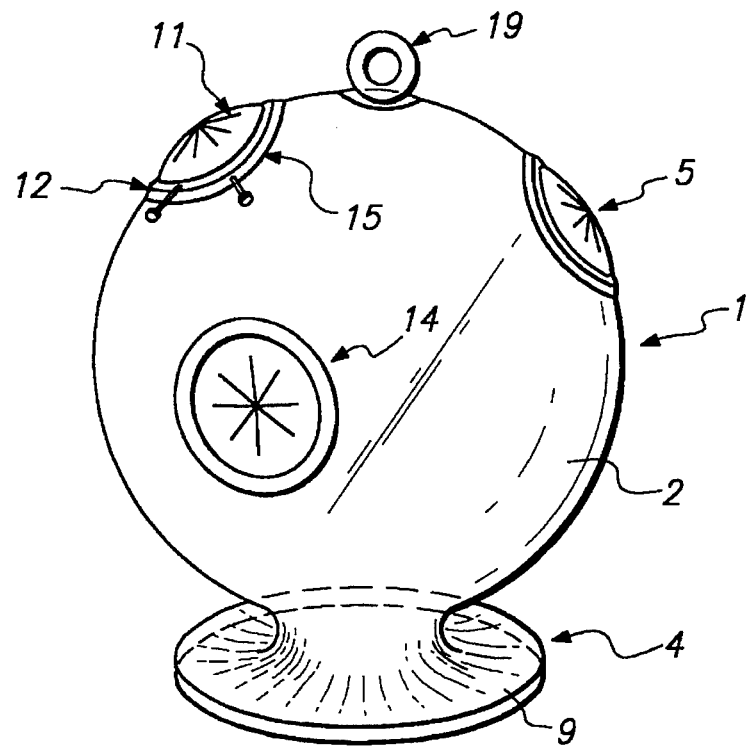
FIG. 5 shows a medical device in accordance with a further embodiment of the invention.

The iris valve 11 may be a fixed iris valve 14 wherein the valve is always biased closed due to the resilient tube 13 which is held in a twisted condition, as shown in FIGS. 1 and 5. The iris valve 11 may also be an adjustable valve 15 wherein one ring is rotatable with respect to the other ring, as shown in FIGS. 1 and 5. The fixed iris construction allows access of relatively small surgical instruments or tools, e.g., 5 to 20 mm diameter, due to the elasticity of the tube material which allows the body of the instrument to be inserted through the center of the iris. A substantially gastight seal is maintained at all times such that the valve sealedly receives the tool or if the valve is large enough a surgeon's hand can be passed therethrough.

Figure 4A:
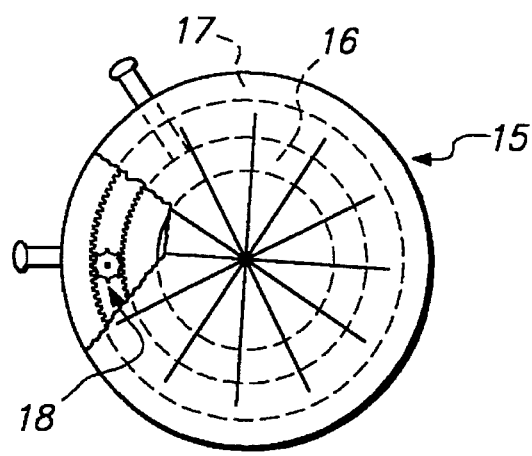
FIGS. 4a–b show details of an adjustable iris valve which can be incorporated in the medical device according to the invention.
Figure 4B:
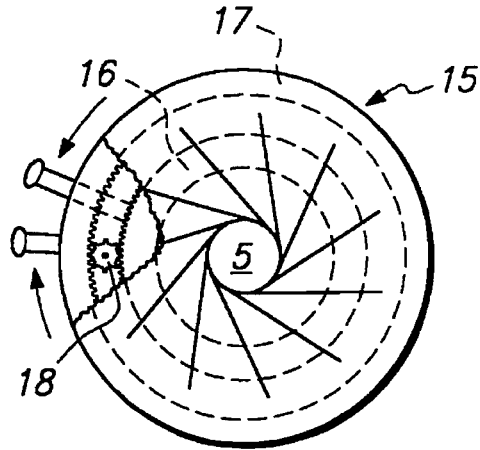

For larger objects, such as a hand, it may be desirable to use the adjustable iris valve 15. In this instance, the valve 15 can be quickly opened wide enough to allow passage of a hand and then closed around the wrist of the surgeon to prevent loss of pneumoperitoneum. For instance, the valve 15 can include an inner ring 16 which rotates relative to a fixed outer ring 17, the rings being separated by one or more gears 18, as shown in FIGS. 4a–b.

Other valve constructions which can be used for the access opening 5 include a re-enterable valve constructed from self-sealing gels. Such gels allow the penetration of objects, yet on withdrawing the invading device they seal behind it as it is withdrawn. Suitable materials include, for example, gels based on lightly cross-linked silicone, vegetable, or fish oils, or blends thereof. A valve somewhat like a multi-leaved flapper valve may also be used. Further, for relatively small diameter instruments, it is possible to use an elastomeric insert which contains a pinhole. This allows access to the interior of the enclosure but such a pinhole type valve could be limited with respect to the size of objects which can pass therethrough yet maintain peritoneum after the objects are removed from the pinhole. Other valving systems such as duck bill valves, etc., may also be used.

It is also possible that a glove-like section may be welded or otherwise attached to the enclosure, rather like a conventional glove box. This would allow the surgeon some access to handle organs or instruments without actually using a valve to access the interior of the enclosure. Additional access for large implements can also be obtained by incorporating a gas tight 'zip fastener' section (such as, for example, commonly found on freezer storage bags). Other possible access valve/port systems are known or would be apparent to those skilled in the art.

The device may further incorporate other features which assist or enhance its performance. For example, a handle 19 can be located on the top of the device, to which the surgeon may apply a lifting force during inflation. Such pulling will bring the deploying means into contact against the inner abdominal wall, thus ensuring a very good seal, and rapid inflation of the "bubble" enclosure by the insufflating gas.

In operation, depending on ambient conditions, it may be further advantageous to coat the inner surface of the "bubble" enclosure with a coating such as a hydrophilic coating. Such coatings could be used to prevent fogging of the device due to condensation of moisture from the abdominal cavity, thus preserving a clear field of view.

According to a further embodiment of the present invention, the enclosure may be rigid, and may or may not require an insufflating gas to deploy it. If a gas is used, the neck section and/or deploying means of the device could be flexible as previously described. For gasless laparoscopic procedures, the neck section of the device could incorporate a retraction section for distension of the trocar puncture site opening.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A medical device for forming an extracorporeal pneumoperitoneum extension comprising an enclosure having an interior and an open end, and deploying means at the open end of the enclosure, the deploying means being deformable to a configuration which permits the open end to pass through a trocar puncture site in an abdominal wall and then expand the open end beneath an inner surface of the abdominal wall such that gas in the abdominal cavity passes into the interior of the enclosure, the enclosure including at least one access opening therein for accessing the interior of the enclosure and allowing surgical operations to be performed beneath the abdominal wall or within the interior of the enclosure.

2. The device of claim 1, wherein the enclosure is bulbous in shape and the deploying means comprises an elastically deformable flange.

3. The device of claim 2, wherein the flange is made of a polyolefin, polyethylene terephthalate, polybutylene terephthalate, polyvinyl chloride, ionomer, polyurethane, nylon, polycarbonate, acrylic, ethylene vinyl acetate copolymer, polyvinylidene fluoride or blend thereof.

4. The device of claim 1, wherein the deploying means comprises an elastically deformable ring surrounding the open end of the enclosure.

5. The device of claim 4, further comprising a constriction between the enclosure and the deploying means.

6. The device of claim 5, wherein the constriction is elastically deformable.

7. The device of claim 5, wherein the enclosure is bulbous in shape at the open end thereof and the constriction forms a narrow passage through which surgical instruments can be inserted into a patient's abdominal cavity.

8. The device of claim 4, wherein the ring is of a springy material selected from the group consisting of engineering polymer, stainless steel, nickel titanium superelastic alloys, or elastomers.

9. The device of claim 1, wherein the deploying means comprises a coil spring.

10. The device of claim 1, wherein the enclosure is of a flexible material selected from the group consisting of a polyolefin, polyethylene terephthalate, polybutylene terephthalate, polyvinyl chloride, ionomer, polyurethane, nylon, polycarbonate, acrylic, ethylene vinyl acetate copolymer, polyvinylidene fluoride or blends thereof.

11. The device of claim 1, wherein the access opening comprises an iris valve.

12. The device of claim 11, wherein the valve is an iris valve having a rotatable ring which adjusts an opening through the valve.

13. The device of claim 11, wherein the iris valve comprises a tube of an elastic material and a pair of rings connected to opposite ends of said tube of elastic material, wherein the tube is twisted to form an air-tight seal.

14. The device of claim 1, wherein the enclosure includes a plurality of access openings at spaced-apart locations on the enclosure.

15. The device of claim 1, further comprising a handle attached to the enclosure.

16. The device of claim 1, wherein the enclosure is transparent.

17. The device of claim 1, wherein the enclosure is gas-tight.

18. The device of claim 1, wherein the enclosure is rigid and self-supporting.

19. The device of claim 1, wherein the enclosure is gas-tight and expandable from a first configuration to a second configuration by supplying pressurized gas to the interior of the enclosure.

20. A medical device for forming an extracorporeal pneumoperitoneum extension comprising an enclosure having an interior and an open end for engaging an opening in an abdominal wall, the enclosure including at least one access opening therein for accessing the interior of the enclosure and allowing surgical operations to be performed beneath the abdominal wall or within the interior of the enclosure, the enclosure being gas-fight and expandable from a first configuration to a second configuration by supplying pressurized gas from the abdominal cavity through the opening in the abdominal wall to the interior of the enclosure.

21. A medical device for forming an extracorporeal pneumoperitoneum extension comprising an enclosure having an interior and an open end, and deploying means at the open end of the enclosure, the deploying means being deformable to a configuration which permits the open end to pass through a trocar puncture site in an abdominal wall and then expand the open end beneath an inner surface of the abdominal wall, the enclosure allowing surgical operations to be performed within the interior of the enclosure, the deploying means comprising an elastically deformable annular flange and the device including an annular gap between the enclosure and the flange, the gap accommodating the abdominal wall surrounding the trocar puncture site when the flange is deployed beneath the inner surface of the abdominal wall.

22. A medical device for forming an extracorporeal pneumoperitoneum extension comprising an enclosure having an interior space and an open end, and deploying means at the open end of the enclosure, the deploying means being deformable to a configuration which permits the open end to pass through a trocar puncture site in an abdominal wall and then expand the open end beneath an inner surface of the abdominal wall, the enclosure including at least one iris valve therein for accessing the interior space of the enclosure and allowing surgical operations to be performed beneath the abdominal wall through the open end or within the interior of the enclosure.

23. The device of claim 22, wherein the iris valve has a rotatable ring which adjusts the size of an opening through the valve.

24. The device of claim 22, wherein the iris valve comprises a tube of an elastic material and a pair of rings connected to opposite ends of said tube of elastic material, wherein the tube is twisted to form an air-tight seal.

* * * * *